United States Patent
Weinstein et al.

(10) Patent No.: US 6,652,838 B2
(45) Date of Patent: *Nov. 25, 2003

(54) METHOD FOR TREATING DIABETES MELLITUS

(76) Inventors: Robert E. Weinstein, 177 Commonwealth Ave., Boston, MA (US) 02116; Allan M. Weinstein, 9205 Pegasus Ct., Potomac, MD (US) 20854

(*) Notice: Subject to any disclaimer, the term of this patent is extended or adjusted under 35 U.S.C. 154(b) by 0 days.

This patent is subject to a terminal disclaimer.

(21) Appl. No.: 10/115,691

(22) Filed: Apr. 4, 2002

(65) Prior Publication Data

US 2002/0146372 A1 Oct. 10, 2002

Related U.S. Application Data

(60) Provisional application No. 60/281,767, filed on Apr. 5, 2001.

(51) Int. Cl.⁷ .............................. A61K 9/12; A61K 9/00; A61K 9/20
(52) U.S. Cl. ........................ 424/45; 424/46; 424/464; 424/400; 128/200.14; 514/866; 514/2
(58) Field of Search ............................ 424/45, 46, 464, 424/400; 128/200.14; 514/866, 2

(56) References Cited

U.S. PATENT DOCUMENTS

| | | | |
|---|---|---|---|
| 6,167,880 B1 * | 1/2001 | Gonda et al. | 128/200.14 |
| 6,187,291 B1 | 2/2001 | Weinstein et al. | |
| 6,447,751 B1 * | 9/2002 | Weinstein et al. | 424/45 |

OTHER PUBLICATIONS

Skyler, Jay S. et al., Efficacy of inhaled human insulin in Type 1 diabetes mellitus; a randomized proof-of-concept study, Lancet 201;357:331–335.

Gale, Edwin A. M., Commentary, Two cheers for inhaled insulin, Lancet 2001;357:324–325.

Cefalu, William T. et al., Inhaled human insulin treatment in patients with Type 2 diabetes mellitus, Annals of Internal Medicine 2001;134:203–207.

Landgraf, Rudiger, Meglitinide analogues in the treatment of Type 2 diabetes mellitus, Drugs and Aging 2000;17(5):411–425.

Moses, Robert G. et al., Flexible meal-related dosing with repaglinide facilitates glycemic control in therapy-naïve Type 2 diabetes, Diabetes Care 2001;24:11–15.

Kalbag, Jyoti B. et al., Mealtime glucose regulation with nateglinide in health volunteers, Diabetes Care 2001;24:73–77.

Lefebvre, Pierre J. et al., Glucose metabolism and the postprandial state, European Journal of Clinical Investigation 1999;29 (Suppl. 2), 1–6.

Kuusisto, J. et al., Prandial glucose regulation and cardiovascular disease in Type 2 diabetes, European Journal of Clinical Investigation 1999;29 (Suppl. 2), 7–11.

Heine, R. J., Current therapeutic options in Type 2 diabetes, European Journal of Clinical Investigation 1999;29 (Suppl. 2), 17–20.

Malaisse, W. J., Repaglinide, a new oral antidiabetic agent: a review of recent preclinical studies, European Journal of Clinical Investigation 1999;29 (Suppl. 2), 21–29.

Owens, D. R., Repaglinide: a new short-acting insulinotropic agent for the treatment of Type 2 diabetes, European Journal of Clinical Investigation 1999;29 (Suppl.2), 30–37.

Massi–Benedetti, M. et al., Cardiovascular risk factors in Type 2 diabetes: the role of hyperglycemia, Exp Clin Endocrinol Diabetes 1999;106 (Suppl. 4)S120–3.

Polonsky, K. S., Evolution of beta–cell dysfunction in impaired glucose tolerance and diabetes, Exp Clin Endocrinol Diabetes 1999;106 (Suppl. 4)S124–7.

Landgraf, R., Approaches to the management of postprandial hyperglycaemia, Exp Clin Endocrinol Diabetes 1999;106 (Suppl. 4)S128–32.

Moses, R., Repaglinide in combination therapy with metformin in Type 2 diabetes, Exp Clin Endocrinol Diabetes 1999;106 (Suppl. 4)S136–9.

Schatz, H., Preclinical and clinical studies on safety and tolerability of repaglinide, Exp Clin Endocrinol Diabetes 1999;106 (Supppl. 4)S144–8.

* cited by examiner

Primary Examiner—Michael G. Hartley
Assistant Examiner—Mina Haghighatian
(74) Attorney, Agent, or Firm—Robert R. Deleault, Esq.; Mesmer & Deleault, PLLC

(57) ABSTRACT

A method for treating postprandial hyperglycemia in diabetes mellitus in a human which employs a combination of an aerosolizable topical insulin and a short-acting oral hypoglycemic agent as a regimen taken adjacent to mealtime.

9 Claims, No Drawings

METHOD FOR TREATING DIABETES MELLITUS

This application claims the benefit of U.S. Provisional Application No. 60/281,767 filed Apr. 5, 2001.

BACKGROUND OF THE INVENTION

1. Field of the Invention

The present invention relates generally to the treatment of diabetes. Particularly, the present invention relates to the treatment of diabetes without the use of insulin injections.

2. Description of the Prior Art

Diabetes mellitus is a chronic illness caused by a lack of an effective amount of insulin. It is manifested by the elevation of blood sugar. Diabetes mellitus is the fourth leading cause of death by disease in the United States and the leading cause of irreversible blindness and chronic renal failure. Treatment for diabetes is directed to lowering blood sugar, particularly after meals, and to preventing long term complications that include neuropathy, accelerated atherosclerosis, myocardial infarction, gangrene of the lower extremities, retinopathy and nephropathy. Diabetic individuals are typically required to comply with treatments over very long periods of time to avoid these complications.

The two pharmacological modalities presently used to lower blood sugar are oral hypoglycemic (anti-diabetic) agents and insulin. Insulin replacement is presently accomplished by injection and is based upon the lack of insulin or limitation of its action in diabetes mellitus. Oral antidiabetic agents are not chemically akin to insulin and their sugar-lowering mechanism differs from the action of direct insulin replacement. Oral hypoglycemic agents and insulin are, at present, therapeutically utilized alone or in concert with each other, according to the needs of the diabetic individual. Some individuals are best treated with more than one oral agent, with, or without insulin.

Oral hypoglycemic agents presently include sulfonylureas, biguanides, alpha-glucosidase inhibitors, and thiazolidinediones. These agents are known to be used alone and in various combinations with each other to lower blood sugar. These oral hypoglycemic agents are considered to be long acting agents, acting over many hours. A side effect of agents acting over long periods is the risk of hypoglycemia if the user forgets or otherwise fails to eat hours after taking the medication. Each of these classes of compounds operates by a different mechanism. For example, sulfonylureas lower blood sugar by stimulating insulin release from pancreatic islet cells. Examples of sulfonylureas include so-called first-generation agents such as tolbutamide, acetohexamide, tolazamide, and chlorpropamide, and second-generation agents such as glyburide, glipizide, and glimeperide. First and second generation sulfonylureas differ in their potency, adverse effects and duration of action.

Metformin, which has an "insulin sparing" action, is an example of a biguanide. Acarabose, which has an action of reducing the rate of carbohydrate absorption, is an example of an alpha-glucosidase inhibitor. Troglitizone, which acts to potentiate the action of insulin (but has been found to cause idiosyncratic liver injury), is an example of the thiazolidinedione class. More recently, an additional class of hypoglycemic agent known as the meglitinides has become available for treatment in the United States. An example of a meglitinide is repaglinide, a carbamoylmethyl benzoic acid derivative.

Like the sulfonylureas, the meglitinides stimulate insulin secretion from pancreatic insulin-producing cells. However, they are chemically distinct and bind to a different receptor. They can be used alone as well as in concert with other oral agents. Repaglinide and nateglinide exhibit the fast-acting characteristics of the meglitinide class including rapid absorption, stimulation of insulin release within a few minutes, and rapid biliary excretion.

Recent clinical studies in diabetic individuals have disclosed that insulin can be administered topically to human membrane surfaces, especially nasal and pulmonary surfaces, and be absorbed. As with injected insulin, oral hypoglycemic medication may be utilized together with insulin administered by aerosol to lower blood sugar.

U.S. Pat. No. 6,187,291, issued Feb. 13, 2001, is an example of a device based on the use of aerosolizable insulin and at least one long-acting, oral, hypoglycemic agent. It teaches a dispensing container which incorporates an aerosolizable topical insulin preparation, at least one oral hypoglycemic agent, and indicia and instructions for their coordinated use as a single therapeutic regimen for treating diabetes mellitus in a human in order to make such regimens more convenient, encourage compliance and minimize error. The action of such topical insulin has been found to be limited compared to injected insulin.

Therefore, what is needed is a method for treating hyperglycemia, particularly postprandial hyperglycemia, in diabetes mellitus in a human. What is further needed is a method for treating postprandial hyperglycemia in diabetes mellitus in a human that does not require the user to eat in accordance with the timing and action of the treatment agents. What is still further needed is a method for treating postprandial hyperglycemia in diabetes mellitus in a human that minimizes the risk of lowering blood sugar to hypoglycemic levels.

SUMMARY OF THE INVENTION

It is an object of the present invention to provide a method for treating postprandial hyperglycemia in diabetes mellitus in a human without resorting to injections. It is another object of the present invention to provide a method for treating postprandial hyperglycemia in diabetes mellitus that does not require the user to eat in accordance with the timing and action of the treatment agents. It is still another object of the present invention to provide a method of treating postprandial hyperglycemia in diabetes mellitus that minimizes the risk of lowering blood sugar to hypoglycemic levels. It is yet another object of the present invention to facilitate treatment by combining topical aerosolized and oral medication together in a heretofore undisclosed manner for treating diabetes mellitus in a human.

The present invention achieves these and other objectives by providing a method for treating postprandial hyperglycemia in diabetes mellitus in a human that employs an aerosolizable topical insulin preparation and an oral hypoglycemic agent having a relatively short duration of action in combination as a regimen. The combining of short-acting topical insulin and short-acting oral hypoglycemic agents from the meglitinide class are particularly suitable for such regimens.

It is to be understood that oral hypoglycemic medications may be in the form of tablet, pill, capsule, caplet, packets or liquids, gels, or solids, some of which may require reconstituting, or any generally recognized oral form of medication. The topical insulin preparation is in a form such as a powder or liquid that is suitable for aerosolization.

DETAILED DESCRIPTION OF THE PREFERRED EMBODIMENT

The following detailed description of the invention is provided to aid those skilled in the art in practicing the present invention, however, it should not be construed to unduly limit the present invention. Variations and modifications may be made by those of ordinary skill in the art without departing from the scope of the present inventive discovery.

Hyperglycemia, and particularly postprandial hyperglycemia, is considered to play an important role in the development of cardiovascular disease in diabetes. Management of hyperglycemia, and particularly postprandial hyperglycemia, is therefore an important objective in diabetes treatment.

The present invention rests on the heretofore undisclosed consideration that blood glucose may be controlled at the time of glucose ingestion in some diabetic individuals with a complementary combination of short-acting anti-diabetic agents administered by separate routes and acting by different mechanisms. Moreover, the envisioned method contemplates achieving this without the need for injections. Another advantage of the method of the present invention is a lessening of the stringent burden of adhering to a strict meal schedule, and diminished risk of hypoglycemia compared to present therapies that employ long-acting agents.

Present treatments for diabetes usually employ long-acting glucose-lowering agents that require the user to eat in accord with the timing and action of these agents. If the user of a long-acting agent fails to eat once such medication is taken, he or she risks lowering his/her blood sugar to hypoglycemic levels, creating morbid as well as mortal risk.

The meglitinides are a new class of secretagogues that stimulate rapid and dose-dependent endogenous insulin release. Repaglinide and nateglinide, members of the meglitinide class, are rapidly absorbed from the intestinal tract. They have a rapid onset of action and rate of elimination making them suitable for meal-related dosing rather than long-acting dosing. Diabetic individuals, however, are known to vary in their response to treatments, and in some individuals, this treatment alone will not suffice to adequately control blood sugar.

It is newly appreciated that insulin is absorbed into the human blood stream through membrane surfaces, for example, by inhalation through the lung. Thus, insulin can be administered in this fashion rather than by injection. Dosed in this manner, insulin is found to have rapid absorption and a rapid onset and duration of action. However, limitations are known on the amount that can be reasonably administered by the topical route resulting in limitations on effect. It is perceived that topical insulin, by virtue of its fast onset of action and short duration of action, may also be utilized for prandial control of hyperglycemia and that such dosing might accomplish flexibility of meal times. Because of limited potency, however, it is appreciated that such treatment might not alone suffice for some diabetics to control hyperglycemia.

For those individuals in whom control of postprandial hyperglycemia cannot be accomplished with either a short acting oral hypoglycemic agent alone, or with inhaled insulin alone, the present invention anticipates that a combination of the two, acting in concert by different mechanisms, can achieve the desired therapeutic effect in some individuals. Further, postprandial control of hyperglycemia would be feasible for such individuals by virtue of the similarly rapid onset of action of both agents. It is additionally contemplated that the potential for hypoglycemia to occur at a later time consequent to medicating is minimized by the similarly short duration of action of both agents.

Costs are an important factor in treatments. It may prove advantageous to employ smaller amounts of one agent of the present invention, if more costly, and complement it therapeutically with a less costly other agent of the present invention.

The following is one example of a treatment method of the present invention. Typically, a diabetic individual would be prescribed an aerosolizable, inhalable insulin and a short-acting oral hypoglycemic agent such as repaglinide accompanied by instructions for their combined use as a regimen. An example of a specific regimen may be to take 2 mg of aerosolized inhaled insulin and 1 mg of oral repaglinide in the time period adjacent to meals. Such period is defined as being within approximately one-half hour before or after eating. Both agents have a rapid onset and short duration of action. Given in this manner, the agents would effect control of blood glucose at the specific time of need. Moreover, this would be accomplished without resorting to injections of insulin. Such a regimen provides greater flexibility of meal times compared to the necessity to eat, that is required when taking long-acting agents, in order to prevent hypoglycemia. Such a regimen carries less risk of developing hypoglycemia that may occur hours after taking the medications compared to treatments with long-acting agents.

Treatment regimens may be refined according to the needs of particular individuals. It may be advantageous to administer the medications at different times adjacent to mealtime. For example, taking the oral dosage before eating and the insulin dose later if then required after blood sugar monitoring. Regimens of the present invention may require utilization of additional other oral anti-diabetic agents and conventional injected insulin, as fits the need of particular diabetic individuals. It is recognized that use of the aforementioned agents together as described is contingent upon the recommendations and indications provided by the manufacturers of the medications, and the recommendations for use by medical caregivers.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A method of regulating postprandial blood sugar in a diabetic individual, said method comprising:

obtaining an aerosolizable topical insulin;

obtaining a short-acting oral hypoglycemic agent having a duration of action shorter than the long-acting oral hypoglycemic agents selected from the group consisting of sulfonylureas, biguanides, alphaglucosidase inhibitors, and thiazolidinediones; and utilizing said aerosolizable insulin and ingesting said oral hypoglycemic agent adjacent to mealtime.

2. The method of claim 1 wherein said short-acting oral hypoglycemic agent is a meglitinide.

3. The method of claim 2 wherein said meglitinide is repaglinide or nateglinide.

4. The method of claim 1 wherein said aerosolizable insulin and said oral hypoglycemic agent are utilized during the time period that is about one-half hour before to about one-half hour after mealtime.

5. A method of regulating postprandial blood sugar in a diabetic individual, said method comprising:

obtaining an aerosolizable topical insulin;

obtaining a short-acting, oral hypoglycemic agent that is a meglitinide; and administering said aerosolizable topical insulin and said short-acting, oral hypoglycemic agent around mealtime.

6. The method of claim 5 wherein said meglitinide is repaglinide or nateglinide.

7. The method of claim 5 wherein said administration step is administered during a time period within about one-half hour before and about one-half hour after mealtime.

8. A method of regulating postprandial blood sugar in a diabetic individual, said method comprising:

obtaining an aerosolizable topical insulin;

obtaining a short-acting, oral hypoglycemic agent that is a meglitinide; and administering said aerosolizable topical insulin and said short-acting, oral hypoglycemic agent within about one-half hour before and about one-half hour after mealtime.

9. The method of claim 8 wherein said meglitinide is repaglinide or nateglinide.

* * * * *